US012232660B2

(12) United States Patent
Tsuboi et al.

(10) Patent No.: US 12,232,660 B2
(45) Date of Patent: Feb. 25, 2025

(54) BATHTUB APPARATUS

(71) Applicant: TOTO LTD., Kitakyushu (JP)

(72) Inventors: Hiroshi Tsuboi, Kitakyushu (JP); Koji Sonoda, Kitakyushu (JP); Kei Watanabe, Kitakyushu (JP); Yu Ichikawa, Kitakyushu (JP); Masayoshi Enoki, Kitakyushu (JP); Kensuke Azuma, Kitakyushu (JP); Ryoko Uno, Kitakyushu (JP); Mao Jinde, Kitakyushu (JP); Yuwa Ishii, Kitakyushu (JP); Kenji Furukawa, Kitakyushu (JP); Hiroki Kurita, Kitakyushu (JP)

(73) Assignee: TOTO LTD., Kitakyushu (JP)

( * ) Notice: Subject to any disclaimer, the term of this patent is extended or adjusted under 35 U.S.C. 154(b) by 100 days.

(21) Appl. No.: 18/014,017

(22) PCT Filed: Jul. 7, 2021

(86) PCT No.: PCT/JP2021/025551
§ 371 (c)(1),
(2) Date: Dec. 30, 2022

(87) PCT Pub. No.: WO2022/009914
PCT Pub. Date: Jan. 13, 2022

(65) Prior Publication Data
US 2023/0284839 A1    Sep. 14, 2023

(30) Foreign Application Priority Data

Jul. 10, 2020  (JP) .................................. 2020-119333
Jul. 10, 2020  (JP) .................................. 2020-119334

(51) Int. Cl.
*A47K 3/022*    (2006.01)
*A61B 5/282*    (2021.01)

(52) U.S. Cl.
CPC .............. *A47K 3/022* (2013.01); *A61B 5/282* (2021.01)

(58) Field of Classification Search
CPC ............................... A47K 3/022; A61B 5/282
(Continued)

(56) References Cited

U.S. PATENT DOCUMENTS

| 5,410,471 A * | 4/1995 | Alyfuku ................. A61B 5/002 |
| | | 600/300 |
| 2008/0163416 A1* | 7/2008 | Go .......................... E03C 1/055 |
| | | 700/65 |
| 2009/0065353 A1* | 3/2009 | Haase .................... A47K 3/022 |
| | | 607/86 |

FOREIGN PATENT DOCUMENTS

JP    02-61307 U    5/1990
JP    05-095921 A    4/1993
(Continued)

OTHER PUBLICATIONS

International Search Report and Written Opinion for PCT/JP2021/025551, mailed Sep. 21, 2021.
(Continued)

*Primary Examiner* — Huyen D Le
(74) *Attorney, Agent, or Firm* — IceMiller LLP

(57) ABSTRACT

There is provided a bathtub apparatus capable of satisfactorily detecting an electrocardiographic signal even in a state where water is being discharged into a bathtub by a water discharge device. The present invention is a bathtub apparatus (1) including a bathtub main body (2), a water discharge device (8) that discharges water toward inside of the bathtub main body and is provided above a first inner wall surface (2a) forming a short side of the bathtub main body, and electrodes (4a, 4b, 4c) attached to the bathtub main body to detect an electrocardiographic signal of a bathing person, where the electrodes are arranged on an inner wall surface
(Continued)

of the bathtub main body, and are arranged closer to the first inner wall surface than a position (P) where water discharged from the water discharge device hits a water surface of the water stored in the bathtub main body.

9 Claims, 8 Drawing Sheets

(58) Field of Classification Search
USPC .......................................................... 4/559
See application file for complete search history.

(56) References Cited

FOREIGN PATENT DOCUMENTS

| | | |
|---|---|---|
| JP | 10-155757 A | 6/1998 |
| JP | 10-179529 A | 7/1998 |
| JP | 2000-70169 A | 3/2000 |
| JP | 2017-209141 A | 11/2017 |

OTHER PUBLICATIONS

Office Action issued in JP Application No. 2020-119333, issued Jan. 11, 2024 (w/translation) [5 pages].

\* cited by examiner

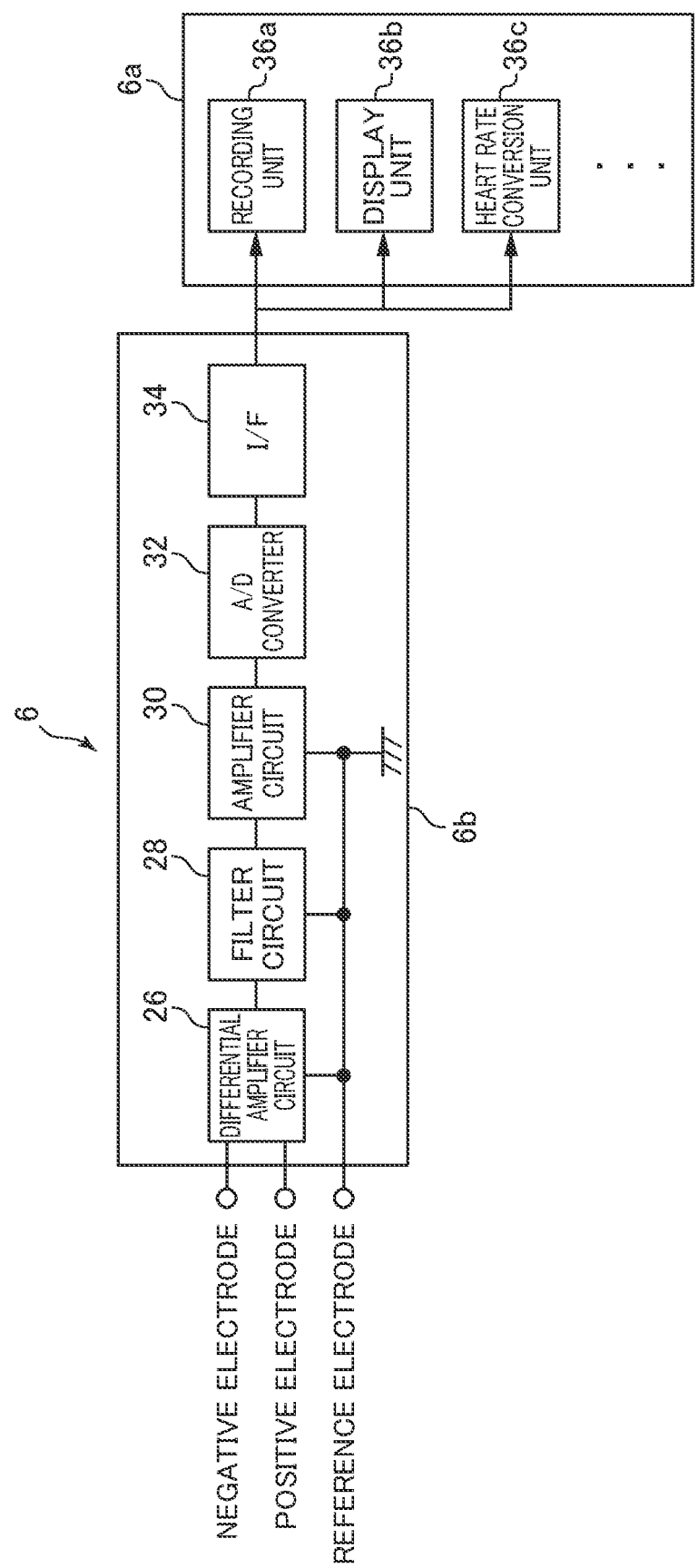

BATHTUB APPARATUS

CROSS-REFERENCE TO RELATED APPLICATIONS

This application is a National Stage of International Patent Application No. PCT/JP2021/025551, filed on Jul. 7, 2021, which claims priority to Japanese Application Nos. 2020-119333 and 2020-119334, both filed on Jul. 10, 2020, the disclosures of which are incorporated by reference in their entireties.

BACKGROUND OF THE INVENTION

Field of the Invention

The present invention relates to a bathtub apparatus, and particularly, to a bathtub apparatus including an electrocardiographic signal detection function.

Description of the Related Art

One takes a bath not just to keep the body clean, but also to refresh the body and mind by warming the body, relaxing and easing stress. Particularly, these days, a bathtub including various amenity functions is becoming widespread in household, and more and more people are enjoying taking a bath. For example, Japanese Patent Laid-Open No. 2017-209141 (Patent Literature 1) describes a bathtub apparatus. The bathtub apparatus includes a flat water discharge part along a top edge portion of a short side of a bathtub, and hot water is discharged from the water discharge part toward shoulders of a bathing person leaning against a wall surface of the bathtub. Accordingly, a massaging effect on the shoulders of the bathing person can be obtained together with a warming effect, and the bathing person can comfortably enjoy taking a bath.

However, the number of accident victims in the bath at home reaches as high as about 20,000, and the number of deaths is on the increase, and most of the deaths occurring in the bath are elderly people. During a bath, the body is warmed by the warming effect and relaxing effect can be obtained, but when bathing time becomes very long, burden is imposed on the heart and the like of the bathing person. Particularly, a bathtub apparatus as described in Patent Literature 1 allows a bathing person to comfortably enjoy taking a bath and tends to increase the bathing time, and it is highly necessary to monitor a health state of the bathing person.

Japanese Patent Laid-Open No. 5-95921 (Patent Literature 2) describes a bathtub electrocardiograph. The bathtub electrocardiograph includes a pair of different electrodes attached to facing surfaces of a bathtub and one indifferent electrode, and signals acquired by the electrodes are transmitted to a main body unit including an electrocardiogram monitor unit and a heart rate display unit. At the main body unit, an electrocardiographic waveform of a bathing person is displayed on the heart rate display unit, and a heart rate of the bathing person is displayed on the heart rate display unit. That is, according to the invention described in Patent Literature 2, the electrodes are arranged such that the heart of the bathing person leaning against an inner wall surface that is a short side of the bathtub is sandwiched between the pair of different electrodes attached to side wall surfaces on both sides of the short side, and an electrocardiographic signal of the bathing person is thus acquired. A health state of the bathing person in the bath may thus be monitored in real time.

Furthermore, Japanese Patent Laid-Open No. 10-179529 (Patent Literature 3) describes an electrocardiogram examination apparatus. The electrocardiogram examination apparatus includes a right electrode and a left electrode on an inner wall surface of a bathtub and acquires an electrocardiogram of a bathing person. Moreover, with the electrocardiogram examination apparatus described in Patent Literature 3, the right electrode is arranged on a backrest surface of the bathtub where the bathing person leans against, and the left electrode is arranged on a side wall surface adjacent to the backrest surface.

Furthermore, Japanese Utility Model Laid-Open No. 2-61307 (Patent Literature 4) describes an underwater electrocardiogram measurement apparatus. With the underwater electrocardiogram measurement apparatus, first induction is obtained by arranging three electrodes on a wall surface of a bathtub, the three electrodes being a negative electrode, a positive electrode, and a neutral point. With the underwater electrocardiogram measurement apparatus described in Patent Literature 4, the electrode as the negative electrode is arranged at an upper part of a side wall surface that is adjacent on a right side of a backrest surface of a bathtub so as to be located near the right shoulder of a bathing person leaning against the backrest surface. Moreover, the electrode as the positive electrode is arranged at a lower part of a facing side wall surface so as to be located near the lower left back of the bathing person, and the electrode as the neutral point is arranged on a surface facing the backrest surface, close to toes of the bathing person.

However, there is a problem that an accurate electrocardiographic signal is not obtained by simply applying the bathtub electrocardiograph described in Patent Literature 2 to the bathtub apparatus including a water discharge device as described in Patent Literature 1. That is, with the electrocardiograph as described in Patent Literature 2, according to which an electrocardiographic signal is acquired by attaching electrodes to a bathtub, the electrocardiographic signal of a bathing person is acquired via water that is stored in the bathtub. On the other hand, in a state where water is being discharged into the bathtub by the water discharge device, air bubbles are generated in the water when the water that is being discharged into the bathtub hits a water surface of the water in the bathtub. Accordingly, the electrocardiographic signal that is detected via the water in the bathtub is affected, and an accurate electrocardiographic signal is difficult to acquire.

Accordingly, the present invention aims to provide a bathtub apparatus that is capable of satisfactorily detecting an electrocardiographic signal even in a state where water is being discharged into a bathtub by a water discharge device.

SUMMARY OF THE INVENTION

To solve the problems as described above, the present invention is a bathtub apparatus capable of detecting an electrocardiographic signal, the bathtub apparatus including: a bathtub main body that is formed into a substantially rectangular shape in plan view; a water discharge device that discharges water toward inside of the bathtub main body, the water discharge device being provided above a first inner wall surface forming a short side of the bathtub main body; and an electrode that is attached to the bathtub main body to detect an electrocardiographic signal of a bathing person via water that is stored in the bathtub main body, where the electrode is arranged on an inner wall surface of the bathtub main body, and is arranged closer to the first inner wall surface than a position where water that is discharged from the water discharge device hits a water surface of the water that is stored in the bathtub main body.

According to the present invention configured in the above manner, the water discharge device is provided above the first inner wall surface of the bathtub main body to discharge water inside the bathtub main body. On the other hand, the electrode to detect the electrocardiographic signal of a bathing person is arranged on an inner wall surface of the bathtub main body, closer to the first inner wall surface than the position where water that is discharged from the water discharge device hits the water surface, and the electrode detects the electrocardiographic signal via the water that is stored in the bathtub main body.

The present inventor was faced with a new technical problem that when a bathtub apparatus including a water discharge device that discharges water toward inside of a bathtub main body was provided with an electrode to detect an electrocardiographic signal, the detected electrocardiographic signal was disturbed by air bubbles generated by water discharge. Accordingly, the present inventor tried providing the electrode at a position away from the water discharge device so that the electrocardiographic signal was not easily affected by water discharge. However, influence of air bubbles was not sufficiently mitigated even when the electrode was installed at a position away from the water discharge device, and also, when the electrode was arranged at a position greatly separated from the water discharge device, the electrocardiographic signal was hard to acquire.

Accordingly, the present inventor changed the approach and tried placing the electrode closer to the water discharge device. Influence of air bubbles generated by water discharge is generally thought to increase as the electrode is placed closer to the water discharge device, but the present inventor found that, in actual use state of the bathtub apparatus, the influence of air bubbles is reduced when the electrode is arranged at a position close to the water discharge device. That is, when water from the water discharge device directly hits the water surface in the bathtub main body, air bubbles generated by hitting of water flows in a direction away from the position hit by the water. Moreover, in the case where water from the water discharge device hits the bathing person and then hits the water surface, air bubbles are hardly generated because the water is adjusted to flow along the body of the bathing person when hitting the bathing person. Accordingly, in the actual use state of the bathtub apparatus, the influence of air bubbles is actually reduced when the electrode is arranged closer to the water discharge device. That is, it was found that, in the actual use state of the bathtub apparatus, the bathing person with respect to whom the electrocardiographic signal is to be detected blocks the flow of air bubbles generated by water discharge, and a region where there are not many air bubbles is generated inside the bathtub.

Through diligent research, the present inventor found that the influence of air bubbles may be sufficiently eliminated by arranging the electrode closer to the first inner wall surface where the water discharge device is provided than the position where the water that is discharged from the water discharge device hits the water surface. According to the present invention configured in the above manner, the electrode is arranged closer to the first inner wall surface than the position where the water that is discharged from the water discharge device hits the water surface of the water that is stored in the bathtub main body. Accordingly, the electrocardiographic signal may be satisfactorily detected also with the bathtub apparatus including the water discharge device that discharges water toward the inside of the bathtub main body.

In the present invention, preferably, the electrode is arranged on the inner wall surface of the bathtub main body, at a predetermined height position, and in a state where the water surface of the water that is stored in the bathtub main body is at the predetermined height position, the electrode is arranged closer to the first inner wall surface than the position where water hits the water surface.

According to the present invention configured in the above manner, because the electrode is arranged at a height position where the entire electrode will be completely underwater, the electrode is always in contact with water that is stored in a bathtub, and the electrode does not come into contact with air even when the water surface is rippled due to being hit by the water that is discharged from the water discharge device that discharges water in a direction of shoulders of the bathing person. Accordingly, a bathtub apparatus that is capable of accurately acquiring an electrocardiographic waveform of the bathing person may be provided.

In the present invention, preferably, the electrode is arranged at a position within 360 mm in a horizontal direction toward the inside of the bathtub main body from a water discharge port of the water discharge device. According to the present invention configured in the above manner, because the electrode is arranged at a position that is within 360 mm from the water discharge port of the water discharge device in the horizontal direction, influence of air bubbles generated by water hitting the water surface may be more reliably suppressed.

In the present invention, preferably, the electrode is arranged on the first inner wall surface. According to the present invention configured in the above manner, because the electrode is arranged on the first inner wall surface, air bubbles generated by hitting of water may be more reliably prevented by the bathing person from coming into contact with the electrode, and influence of the air bubbles may be suppressed as much as possible.

Furthermore, the present invention is a bathtub apparatus capable of detecting an electrocardiographic signal, the bathtub apparatus including: a bathtub main body that is formed into a substantially rectangular shape in plan view; and electrodes that are attached to the bathtub main body to detect an electrocardiographic signal of a bathing person via water that is stored in the bathtub main body, where the electrodes are a pair of electrodes including a positive electrode and a negative electrode, and each of the pair of electrodes is arranged on a first inner wall surface forming a short side of the bathtub main body, and the positive electrode and the negative electrode are arranged at respective positions on a left side and a right side of a center line passing through a center of the first inner wall surface in a horizontal direction.

According to the present invention configured in the above manner, because the pair of electrodes including the positive electrode and the negative electrode is arranged on the first inner wall surface forming a short side of the bathtub main body, a distance between the bathing person and each electrode does not become excessively great even in the case of application to a large bathtub main body, and an electrocardiographic signal with sufficient amplitude may be detected.

In the present invention, preferably, a reference electrode to detect a reference potential is further included, the reference electrode being arranged on the first inner wall surface. Because the electrocardiographic signal is detected as a small potential difference between the positive electrode and the negative electrode, acquiring a reference potential is desirable in securing S/N ratio of a detection signal. According to the present invention configured in the above manner, because the reference electrode is also arranged on the first inner wall surface where the positive electrode and the negative electrode are arranged, surfaces where the electrodes are arranged may be put together into one surface, and electric wiring connected to each electrode may be shortened, and S/N ratio of the detection signal may be improved. Moreover, because the electrodes are assembled and attached to the first inner wall surface, ease of assembly at the time of manufacturing the bathtub main body may be increased, and ease of maintenance may also be increased.

In the present invention, preferably, the positive electrode and the negative electrode are each arranged on the first inner wall surface, away from the center line in a left-right direction. In the present invention, the positive electrode and the negative electrode are arranged on the first inner wall surface of the bathtub main body, and also in this case, the positive electrode and the negative electrode need to be arranged on both sides of the heart of the bathing person. Furthermore, when a distance between the positive electrode and the negative electrode is too small, a potential difference generated between the positive electrode and the negative electrode becomes small, and an electrocardiographic signal with sufficient amplitude cannot be acquired. According to the present invention configured in the above manner, because the positive electrode and the negative electrode are each arranged away from the center line, the positive electrode and the negative electrode may be arranged on both sides of the heart of the bathing person leaning against the first inner wall surface of the bathtub main body, and an electrocardiographic signal with sufficient amplitude may be acquired.

In the present invention, preferably, a distance between the positive electrode and the negative electrode in the left-right direction is 700 mm or less. The electrocardiographic signal that is acquired by the positive electrode and the negative electrode is affected by weight of the bathing person or electrical conductivity of water stored in the bathtub main body. That is, in the case where the weight of the bathing person is small, or electrical conductivity of water that is stored is great (depending on water quality in each region or use of bath powder, for example), if the distance between the positive electrode and the negative electrode is not appropriate, an electrocardiographic signal with sufficient amplitude cannot be acquired. According to the present invention configured in the above manner, because the distance between the positive electrode and the negative electrode in the left-right direction is 700 mm or less, an electrocardiographic signal with sufficient amplitude may be acquired in relation to a regular bathing person or normal electrical conductivity of water.

In the present invention, preferably, a distance between the positive electrode and the negative electrode in the left-right direction is 380 mm or more. In the present invention, the positive electrode and the negative electrode are provided on the first inner wall surface of the bathtub main body, and thus, a bathing person leaning against the first inner wall surface possibly comes into contact with the electrode. When the bathing person comes into contact with the electrode, potential of the electrode may be drastically changed, thereby causing a baseline of the electrocardiographic signal to greatly fluctuate, and detection performance for R wave in the electrocardiographic signal, or in other words, detection performance for heart rate of the bathing person, is greatly reduced. Through diligent research on this new technical problem, the present inventor has found that setting the distance between the positive electrode and the negative electrode in the left-right direction to 380 mm or more may greatly reduce the possibility of contact between the back of the bathing person and the electrode. That is, in relation to about 95% of bathing persons who are grown-ups, a contact width of the back of the bathing person with the inner wall surface of the bathtub main body was found to be less than 380 mm. Accordingly, by setting the distance between the positive electrode and the negative electrode in the left-right direction to 380 mm or more, a regular bathing person may be effectively prevented from coming into contact with the electrodes when the bathing person leans against the first inner wall surface with a normal posture.

With the bathtub apparatus of the present invention, an electrocardiographic signal may be satisfactorily detected even in a state where water is being discharged into a bathtub by a water discharge device.

BRIEF DESCRIPTION OF THE DRAWINGS

FIG. 5A is a block diagram showing processing on a signal acquired by electrodes of the bathtub apparatus according to the embodiment of the present invention;

DETAILED DESCRIPTION OF THE PREFERRED EMBODIMENT

Figure 1:
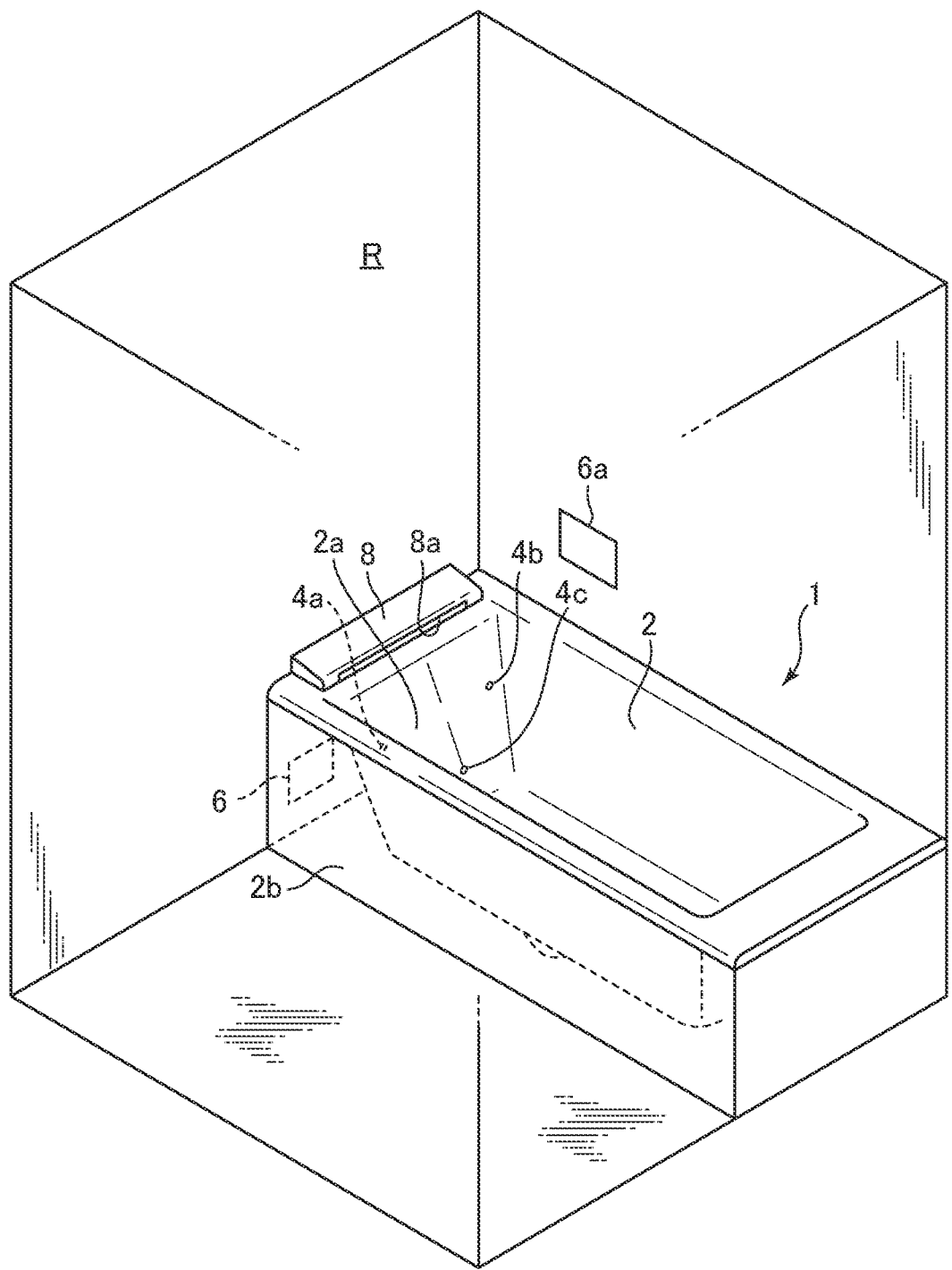
FIG. 1 is a perspective view showing an entire bathroom where a bathtub apparatus according to an embodiment of the present invention is installed.
Figure 2:
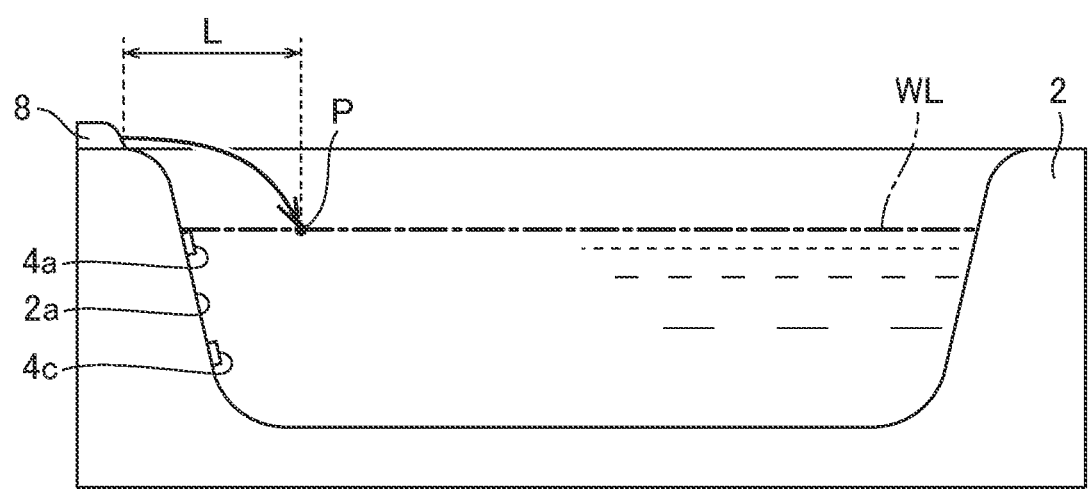
FIG. 2 is a cross-sectional view of the bathtub apparatus according to the embodiment of the present invention.
Figure 3:
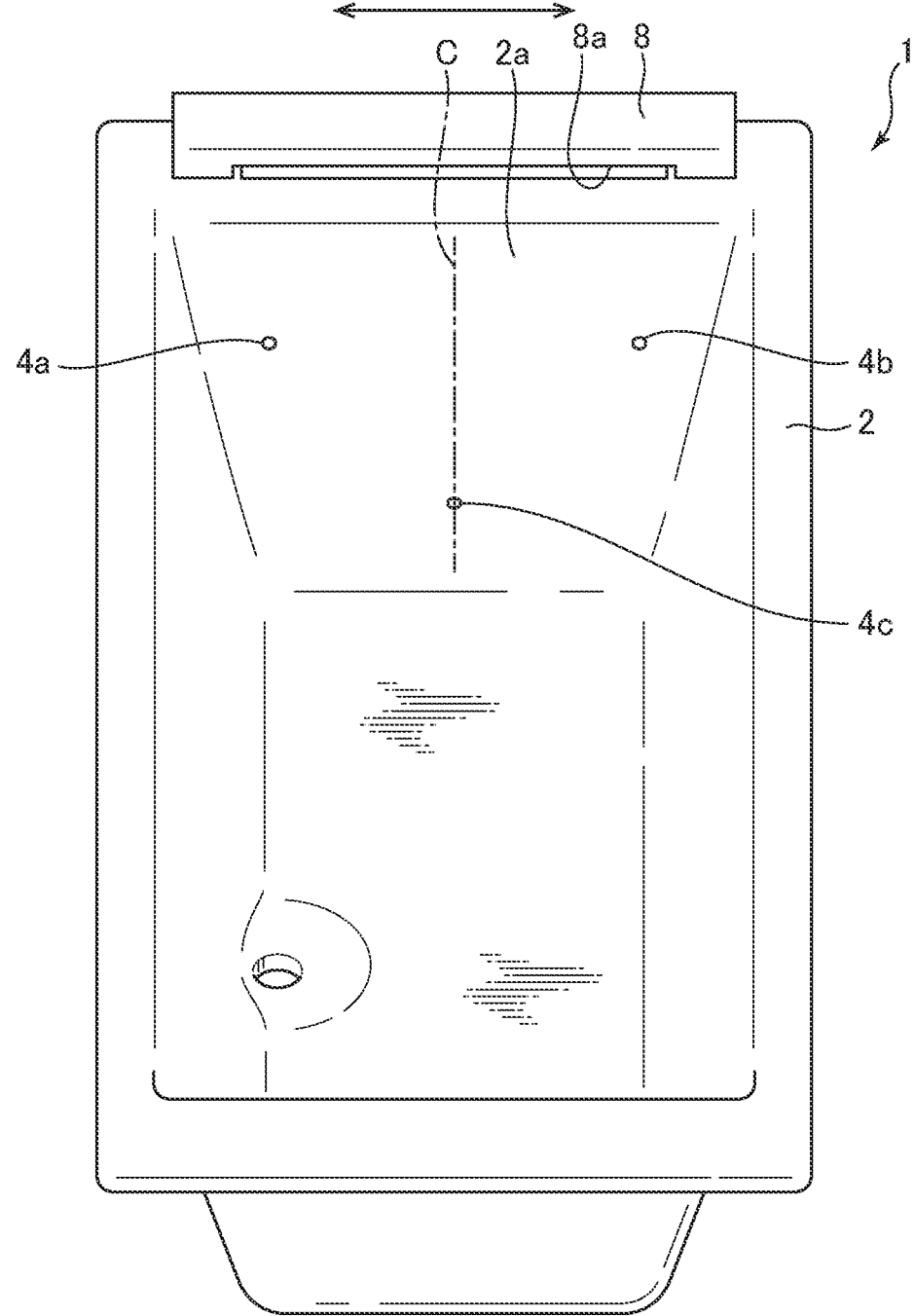
FIG. 3 is a perspective view of the bathtub apparatus according to the embodiment of the present invention seen from obliquely above.
Figure 4:
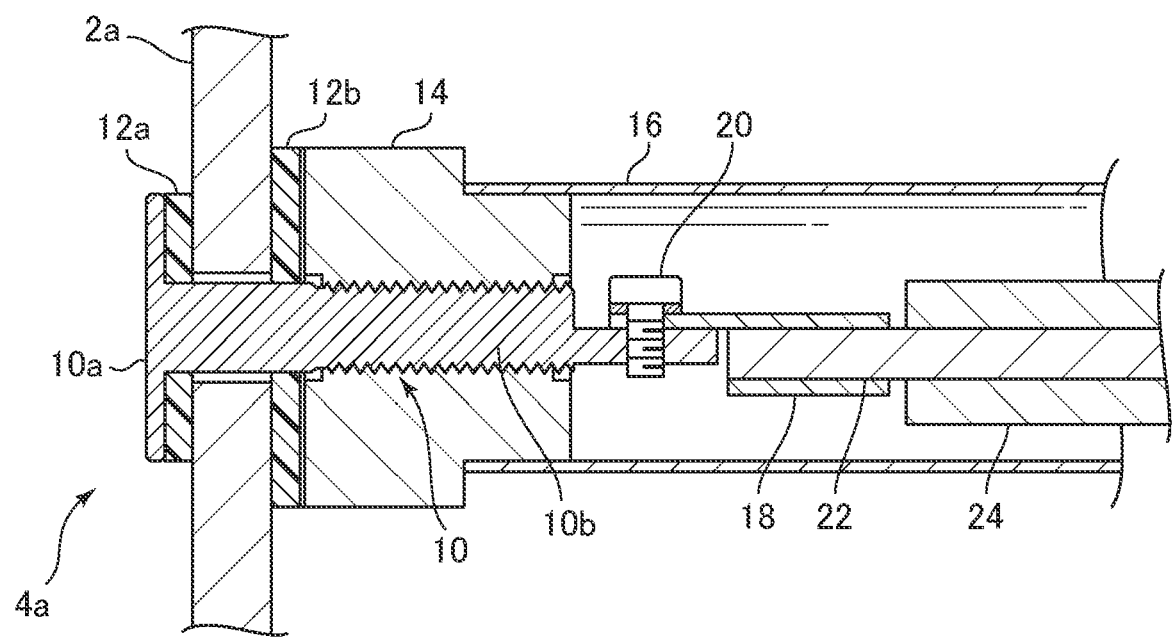
FIG. 4 is a cross-sectional view showing a structure of an electrode provided on the bathtub apparatus according to the embodiment of the present invention.
Figure 5B:
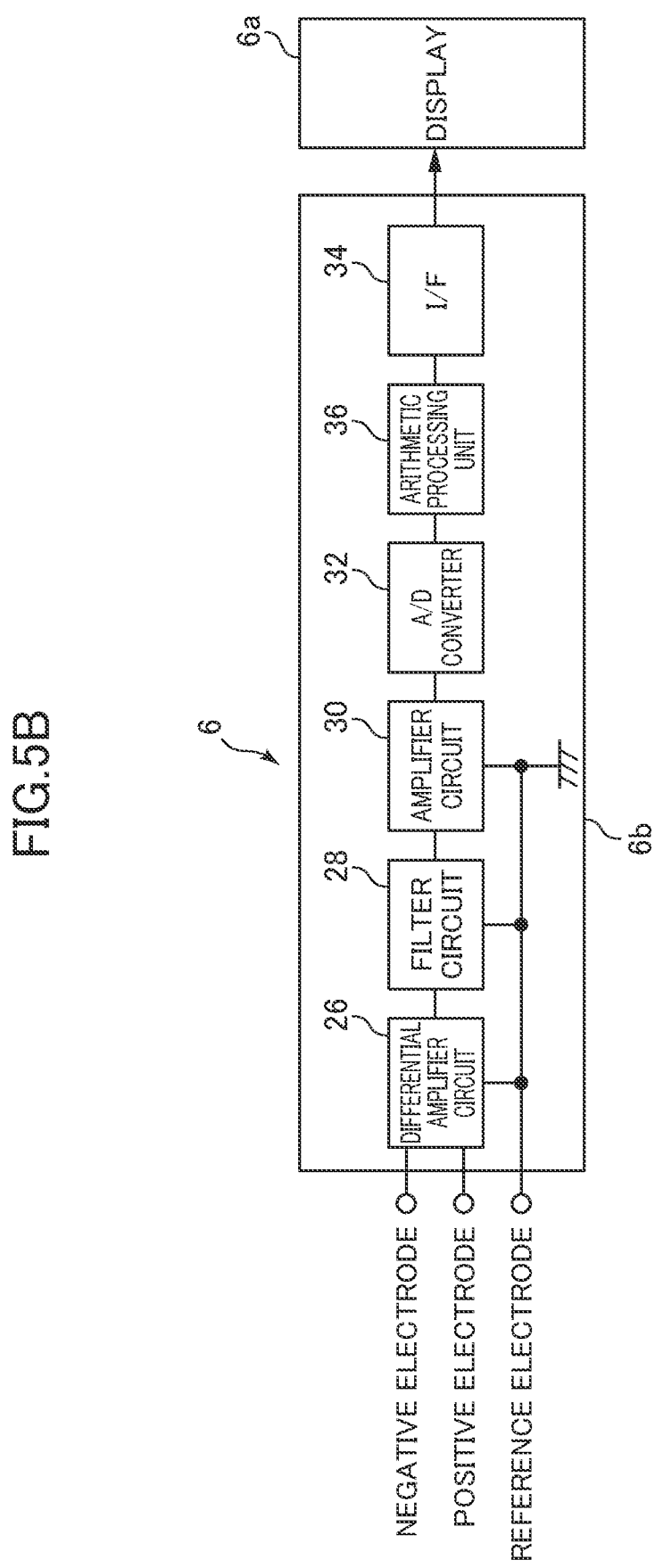
FIG. 5B is a block diagram showing a modification of processing on the signal acquired by the electrodes of the bathtub apparatus according to the embodiment of the present invention.

Next, a bathtub apparatus according to an embodiment of the present invention will be described with reference to the appended drawings. FIG. 1 is a perspective view showing an entire bathroom where the bathtub apparatus according to the embodiment of the present invention is installed. FIG. 2 is a cross-sectional view of the bathtub apparatus according to the embodiment of the present invention. FIG. 3 is a perspective view of the bathtub apparatus according to the embodiment of the present invention seen from obliquely above. FIG. 4 is a cross-sectional view showing a structure of an electrode provided on the bathtub apparatus according to the embodiment of the present invention. FIGS. 5A and 5B are each a block diagram showing processing on a signal acquired by electrodes of the bathtub apparatus according to the embodiment of the present invention.

As shown in FIG. 1, a bathtub apparatus 1 of the embodiment of the present invention includes a bathtub main body 2, a negative electrode 4a, a positive electrode 4b, and a reference electrode 4c attached to the bathtub main body 2, a signal processing apparatus 6 for processing a signal acquired by the electrodes, and a water discharge device 8 provided at a top edge of the bathtub main body 2, and the bathtub apparatus 1 is installed in a bathroom R. Furthermore, a remote control 6a is attached to a wall surface of the bathroom R, and an electrocardiographic signal detection function of the bathtub apparatus 1 and the water discharge device 8 may be operated by the remote control 6a. Furthermore, in the present embodiment, the bathtub apparatus 1 is arranged on one side of the bathroom R, in contact with wall surfaces.

The bathtub main body 2 is formed into a substantially rectangular box in plan view, and stores water inside. In the present embodiment, the bathtub main body 2 is arranged with all of one long side and two short sides on both sides of the long side in contact with inner wall surfaces of the bathroom R. Moreover, an inner wall surface forming one short side of the bathtub main body 2 is formed as a backrest surface 2a that is a first inner wall surface that is formed to allow a bathing person to lean against. Moreover, an apron 2b is detachably attached to a long side of the bathtub main body 2 on a side not in contact with the inner wall surface of the bathroom R. The backrest surface here is an inner wall surface that comes into contact with the back of the bathing person taking a bath. A shape of the backrest surface does not have to be strictly flat and may be a substantially flat surface including a gradually curving curved surface or the like, or may be a shape including a step or irregularities at a part thereof. Furthermore, a shape of the bathtub main body is, but not limited to be, substantially rectangular, and may take any shape where a short side forming the backrest surface includes a straight part or a gentle curve in plan view. For example, a substantially rectangular shape including a gently curved side may be adopted. Moreover, a side facing the backrest surface may take any shape.

The water discharge device 8 is provided above the backrest surface 2a of the bathtub main body 2 to discharge water toward inside of the bathtub main body 2 (toward the short side opposite the backrest surface 2a). As shown in FIG. 2, in the present embodiment, the water discharge device 8 includes a water discharge port 8a that is flat and wide and that extends along a top edge of the backrest surface 2a, and the water discharge device 8 discharges water toward shoulders of a bathing person leaning against the backrest surface 2a. Furthermore, the water discharge device 8 includes a pump (not shown) for sucking in water that is stored in the bathtub main body 2 and for discharging the water from the water discharge port 8a. Accordingly, water in the bathtub main body 2 circulates by being sucked in by the pump (not shown) and by being discharged from the water discharge port 8a to flow into the bathtub main body 2.

Furthermore, in the present embodiment, the water discharge port 8a of the water discharge device 8 is formed to be flat and wide, and thus, water that is discharged from the water discharge port 8a is discharged as a wide, strip-shaped water film that hits a water surface of the water stored in the bathtub main body 2 at a position away from the backrest surface 2a. Moreover, in the present embodiment, the water discharge device 8 is capable of switching pressure strength of the pump (not shown) among three stages of "high", "medium", and "low".

As shown in FIG. 2, in a "high" mode, water is discharged from the water discharge port 8a at a flow rate of about 65 L/min, and the water that is discharged hits a water surface WL in the bathtub main body 2 at a position that is horizontal distance L=about 360 mm away from the water discharge port 8a. Additionally, the water that is discharged from the water discharge port 8a falls along a parabola, and hits the water surface WL at a water-hitting position P. The horizontal distance L mentioned above indicates a distance to the water-hitting position P where a reference amount of water is stored in the bathtub main body 2 and the water surface WL is at a height of about 300 mm from a bottom of the bathtub main body 2. In the same manner, in a "medium" mode, water is discharged at a flow rate of about 55 L/min to hit the water surface at a position that is horizontal distance L=about 310 mm away from the water discharge port 8a, and in a "low" mode, water is discharged at a flow rate of about 49 L/min to hit the water surface at a position that is horizontal distance L=about 280 mm away from the water discharge port 8a. Additionally, these water-hitting positions take numerical values that are measured in a state where the water surface of the water in the bathtub main body 2 is at the height of about 300 mm from the bottom of the bathtub main body 2. The water-hitting position here is a position where the water that is discharged from the water discharge port as a strip-shaped water film hits the water surface of the water stored in the bathtub main body, and does not include hitting of water at a position that is offset from an originally intended position, such as a splash of water discharged from the water discharge port and water flowing from the water discharge port along the inner wall surface.

As shown in FIG. 3, the negative electrode 4a and the positive electrode 4b are a pair of electrodes attached to the bathtub main body 2 to detect an electrocardiographic signal of the bathing person via water that is stored in the bathtub main body 2. The electrocardiographic signal of the bathing person is acquired as a signal about a potential difference between the negative electrode 4a and the positive electrode 4b. The pair of electrodes including the negative electrode 4a and the positive electrode 4b is arranged on the backrest surface 2a forming a short side of the bathtub main body 2. Moreover, the reference electrode 4c is an electrode for acquiring a reference potential of potential detected by the negative electrode 4a and the positive electrode 4b, and this electrode is also arranged on the backrest surface 2a of the bathtub main body 2. The negative electrode 4a, the positive electrode 4b, and the reference electrode 4c are preferably arranged at positions within 360 mm in a horizontal direction from the water discharge port 8a of the water discharge device 8 such that the electrodes 4a to 4c face the inside of the bathtub main body 2.

As described above, with the bathtub apparatus 1 of the present embodiment, all the electrodes for acquiring the electrocardiographic signal are arranged on one backrest surface 2a. That is, each electrode is arranged on the inner wall surface of the bathtub main body 2, on a surface of the backrest surface 2a that is a side closer to the backrest surface 2a than a position where water that is discharged from the water discharge device 8 hits the water surface WL of water that is stored in the bathtub main body 2. In other words, with the bathtub apparatus 1 of the present embodiment, the electrocardiographic signal is detected by only the electrodes that are arranged on one backrest surface 2a.

Furthermore, as shown in FIG. 3, the negative electrode 4a and the positive electrode 4b are arranged along a horizontal direction (left/right) across a center line C in the horizontal direction (width direction) of the backrest surface 2a, at positions that are left-right symmetric across the center line C. That is, the negative electrode 4a and the positive electrode 4b are each arranged on the backrest surface 2a while being separated from the center line C in the horizontal direction (left-right direction), and in the present embodiment, the negative electrode 4a and the positive electrode 4b are arranged while being separated by about 380 mm in the horizontal direction. Furthermore, the negative electrode 4a and the positive electrode 4b are each arranged at a height position of about 300 mm from a bottom surface of the bathtub main body 2 so as to be positioned below the water surface in the bathtub main body 2. That is, when the water surface WL in the bathtub main body 2 is at the height position of about 300 mm, the negative electrode 4a and the positive electrode 4b are positioned entirely below the water surface WL. The negative electrode 4a and the positive electrode 4b may be attached at height positions that are below the water surface in the bathtub main body 2 and that are higher than the reference electrode 4c. The negative electrode 4a and the positive electrode 4b are preferably arranged at height positions that are about 150 mm to about 450 mm from the bottom surface, at positions slightly below a height of the water surface in the bathtub main body 2 under normal use of the bathtub apparatus 1.

For its part, the reference electrode 4c is arranged on the center line C of the backrest surface 2a, at a position lower than the negative electrode 4a and the positive electrode 4b. In the present embodiment, the reference electrode 4c is arranged at a height position of about 150 mm from the bottom surface of the bathtub main body 2 so as to be positioned below the water surface in the bathtub main body 2. Moreover, the reference electrode 4c does not necessarily have to be included and may be omitted.

Next, a structure of each electrode will be described with reference to FIG. 4. Additionally, a structure of the negative electrode 4a is given below, but in the present embodiment, the negative electrode 4a, the positive electrode 4b, and the reference electrode 4c all have the same structure.

As shown in FIG. 4, the negative electrode 4a includes an electrode portion 10, front packing 12a, rear packing 12b, a flange 14, a moistureproof tube 16, a connection terminal 18, a fixing screw 20, an electric lead 22, and a sheath 24. The negative electrode 4a is attached exposed on the surface of the backrest surface 2a of the bathtub main body 2, and watertightness between the negative electrode 4a and the backrest surface 2a is maintained by packing.

The electrode portion 10 is a part that is made of conductive metal and is formed from a disc portion 10a formed into a disc shape, and an axial portion 10b protruding perpendicularly from a rear surface of the disc portion 10a. The disc portion 10a is a thin, disc-shaped part, and a front surface of the disc portion 10a is exposed on the surface of the backrest surface 2a to detect potential. That is, in the present embodiment, the disc portion 10a is formed to have a diameter of about 15 mm and a thickness of about 2.5 mm, and the disc portion 10a is entirely arranged on the surface of the backrest surface 2a. The axial portion 10b is a round-bar portion extending at a right angle from a center of the rear surface of the disc portion 10a, and the axial portion 10b protrudes on a rear side of the backrest surface 2a through a through hole formed in the backrest surface 2a. Furthermore, external screw threads are formed on an intermediate part of the axial portion 10b, and a fixing part for fixing the connection terminal 18 is formed at a tip end part.

The front packing 12a is a disc-shaped member made of rubber, and a circular hole for passing the axial portion 10b of the electrode portion 10 is formed at a center. The front packing 12a has a substantially same diameter as the disc portion 10a of the electrode portion 10 and is arranged on a rear surface side of the disc portion 10a. In a state where the negative electrode 4a is attached to the backrest surface 2a, the front packing 12a is sandwiched between the rear surface of the disc portion 10a and the surface of the backrest surface 2a, and watertightness is thus maintained between the backrest surface 2a and the negative electrode 4a.

The rear packing 12b is a disc-shaped member made of rubber, and a circular hole for passing the axial portion 10b of the electrode portion 10 is formed at a center. The rear packing 12b has a substantially same diameter as a large diameter portion of the flange 14 that is larger than the front packing 12a and is arranged on a rear surface side of the backrest surface 2a. In a state where the negative electrode 4a is attached to the backrest surface 2a, the rear packing 12b is sandwiched between a rear surface of the backrest surface 2a and an end surface of the flange 14, and watertightness is thus maintained between a surface on a rear side of the backrest surface 2a and the negative electrode 4a. Additionally, the front packing 12a and the rear packing 12b may alternatively be made of resin.

The flange 14 is a stepped columnar member including the large diameter portion and a small diameter portion, and internal screw threads for allowing the axial portion 10b of the electrode portion 10 to penetrate is formed at a center. The large diameter portion of the flange 14 is formed to have a substantially same diameter as the rear packing 12b, and the small diameter portion is formed on a rear surface side of the large diameter portion. When the internal screw threads formed to penetrate the flange 14 are screwed and fastened with the external screw threads formed on the axial portion 10b of the electrode portion 10, the rear packing 12b is pressed against the rear surface of the backrest surface 2a by an end surface on a large diameter portion side of the flange 14, and watertightness is thereby maintained.

The moistureproof tube 16 is a thin, long tube made of rubber, and is arranged to cover a tip end of the axial portion 10b of the electrode portion 10, the connection terminal 18, the electric lead 22 and the like. The small diameter portion of the flange 14 is fitted in a tip end of the moistureproof tube 16, and moisture is thus prevented from entering the moistureproof tube 16. Additionally, the moistureproof tube 16 may alternatively be made of resin.

The connection terminal 18 is a part that is made of conductive metal and is connected by pressure-bonding to a tip end of the electric lead 22. A hole for passing the fixing screw 20 is provided in a tip end portion of the connection terminal 18, and the connection terminal 18 may be fixed to the electrode portion 10 by causing the fixing screw 20 passing through the hole to be screwed with an internal screw provided in the tip end of the axial portion 10*b* of the electrode portion 10. The electrode portion 10 and the electric lead 22 may thus be electrically and detachably connected.

The electric lead 22 is a conductive wire for electrically connecting the electrode portion 10 and the signal processing apparatus 6 (FIG. 1), and the electric lead 22 extends from the negative electrode 4*a* to the signal processing apparatus 6. Furthermore, the sheath 24 that is made of insulating material covers the electric lead 22, and electrical insulation of the electric lead 22 is thereby maintained. In the present embodiment, the electric lead 22 extending from each of the negative electrode 4*a*, the positive electrode 4*b*, and the reference electrode 4*c* is connected to the signal processing apparatus 6, and the electrocardiographic signal is thereby input to the signal processing apparatus 6.

Next, a configuration of the signal processing apparatus 6 will be described with reference to FIG. 5A. The signal processing apparatus 6 is an electric circuit to which the negative electrode 4*a*, the positive electrode 4*b*, and the reference electrode 4*c* are connected, and is arranged on the rear surface side of the backrest surface 2*a* of the bathtub main body 2. A signal acquired by the negative electrode 4*a*, the positive electrode 4*b*, and the reference electrode 4*c* is processed by the signal processing apparatus 6, and a processing result is displayed on the remote control 6*a* arranged in the bathroom R and/or a display device (not shown) arranged outside the bathroom R.

As shown in FIG. 5A, the signal processing apparatus 6 includes a differential amplifier circuit 26, a filter circuit 28, an amplifier circuit 30, an A/D converter 32, and an interface circuit 34, and these circuits are embedded inside a housing 6*b*. The differential amplifier circuit 26 is an amplifier circuit to which the electric lead 22 extending from each of the negative electrode 4*a* and the positive electrode 4*b* is connected, and the differential amplifier circuit 26 amplifies a differential voltage between the negative electrode 4*a* and the positive electrode 4*b*.

The differential voltage amplified by the differential amplifier circuit 26 is input to the filter circuit 28, and the filter circuit 28 removes components in an unnecessary frequency band such as ham and passes signal components in a necessary frequency band. A signal from which components in an unnecessary frequency band such as ham are removed by the filter circuit 28 is input to the amplifier circuit 30, and the amplifier circuit 30 amplifies the signal that is input. Moreover, the electric lead 22 extending from the reference electrode 4*c* is connected to ground of the differential amplifier circuit 26, the filter circuit 28, and the amplifier circuit 30.

The A/D converter 32 converts an analog signal amplified by the amplifier circuit 30 into a digital signal. The digital signal that is obtained by A/D conversion by the A/D converter 32 is input to the interface circuit 34, and the interface circuit 34 transmits the input digital signal to the remote control 6*a* (FIG. 1) and/or the external display device (not shown) or the like. A recording unit 36*a*, a display unit 36*b*, a heart rate conversion unit 36*c* and the like are embedded, as an arithmetic processing unit, in the remote control 6*a*. A signal that is transmitted from the signal processing apparatus 6 is recorded in the recording unit 36*a*, and an electrocardiographic waveform of the bathing person is displayed as a graph on the display unit 36*b*. Furthermore, the heart rate conversion unit 36*c* calculates heart rate of the bathing person based on the signal transmitted from the signal processing apparatus 6, and the heart rate of the bathing person that is calculated is displayed on the display unit 36*b* in the form of a numerical value. Furthermore, the electrocardiographic waveform and the heart rate of the bathing person may also be displayed on the display device (not shown) outside the bathroom R, and a health state of the bathing person may thereby be monitored from outside the bathroom R. The present invention may alternatively be configured such that the recording unit 36*a* and the heart rate conversion unit 36*c* are embedded in the display device (not shown) outside the bathroom R.

The electric lead 22 extending from each electrode, and the signal processing apparatus 6 to which the electric leads 22 are connected are all housed in a space on a rear side of the backrest surface 2*a* of the bathtub main body 2. As shown in FIG. 1, the space on the rear side of the backrest surface 2*a* may be accessed from a wash place side in the bathroom R by removing the apron 2*b* of the bathtub main body 2. Accordingly, maintenance of each electrode and the signal processing apparatus 6, such as adjustment and repair, may be easily performed simply by removing the apron 2*b* of the bathtub main body 2. That is, ease of maintenance may be increased by collectively arranging the negative electrode 4*a*, the positive electrode 4*b*, the reference electrode 4*c*, and the signal processing apparatus 6 in a space that can be easily accessed.

Furthermore, as a modification, an arithmetic processing unit 36 may be arranged inside the signal processing apparatus 6, as shown in FIG. 5B. That is, in the modification shown in FIG. 5B, the digital signal that is obtained by conversion by the A/D converter 32 is input to the arithmetic processing unit 36 to be recorded therein, and moreover, the heart rate of the bathing person is calculated. The heart rate that is calculated and the electrocardiographic waveform are transmitted to the remote control 6*a* via the interface circuit 34 and are displayed on a display unit of the remote control 6*a*. Furthermore, the present invention may alternatively be configured such that the heart rate and the electrocardiographic waveform are displayed on the display device (not shown) outside the bathroom R.

Figure 6:
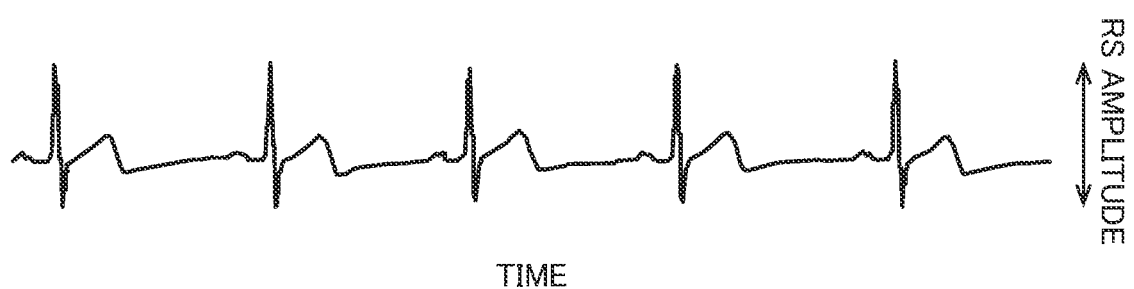
FIG. 6 is a diagram showing an example of an electrocardiographic signal measured by the bathtub apparatus according to the embodiment of the present invention.
Figure 7:
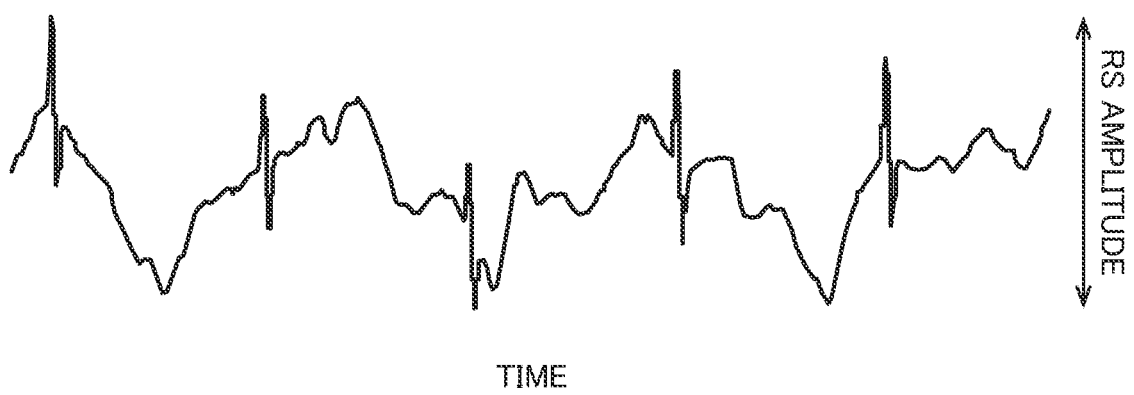
FIG. 7 is a diagram showing, as a comparative example, an example of an electrocardiographic signal that is affected by air bubbles.
Figure 8:
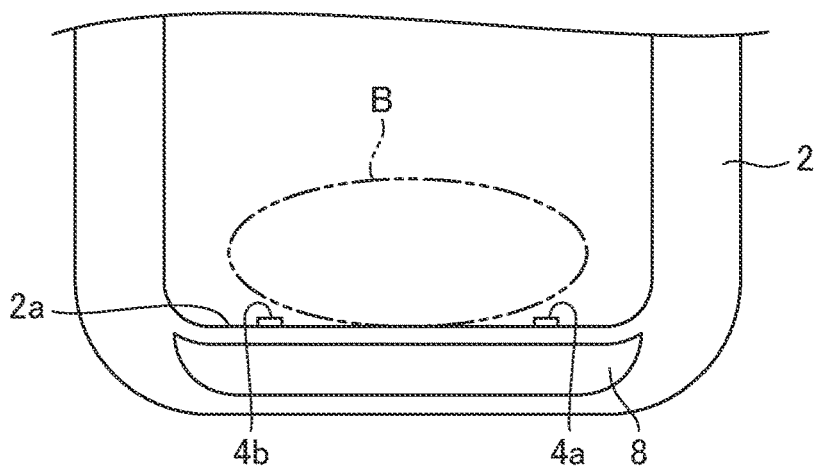
FIG. 8 is a diagram schematically showing a positional relationship between a body of a bathing person leaning against a backrest surface of a bathtub main body and each electrode attached to the backrest surface in the bathtub apparatus according to the embodiment of the present invention.
Figure 9:
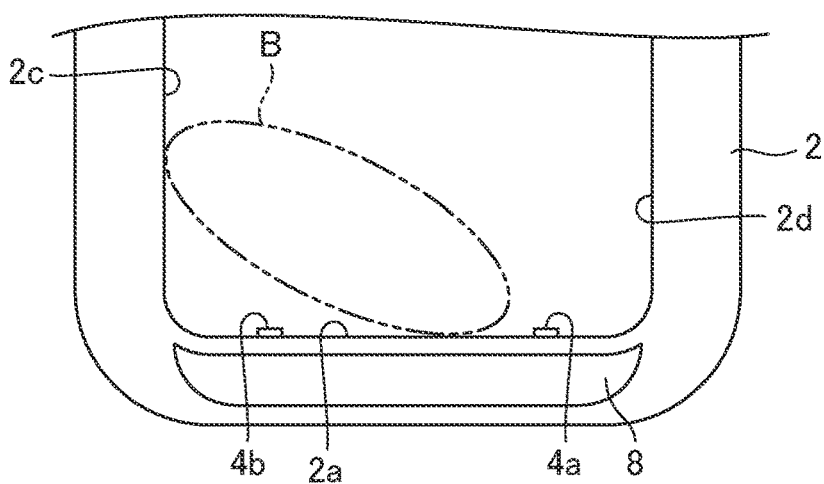
FIG. 9 is a diagram schematically showing a positional relationship between the body of the bathing person leaning against the backrest surface of the bathtub main body and each electrode attached to the backrest surface in the bathtub apparatus according to the embodiment of the present invention.
Figure 10:
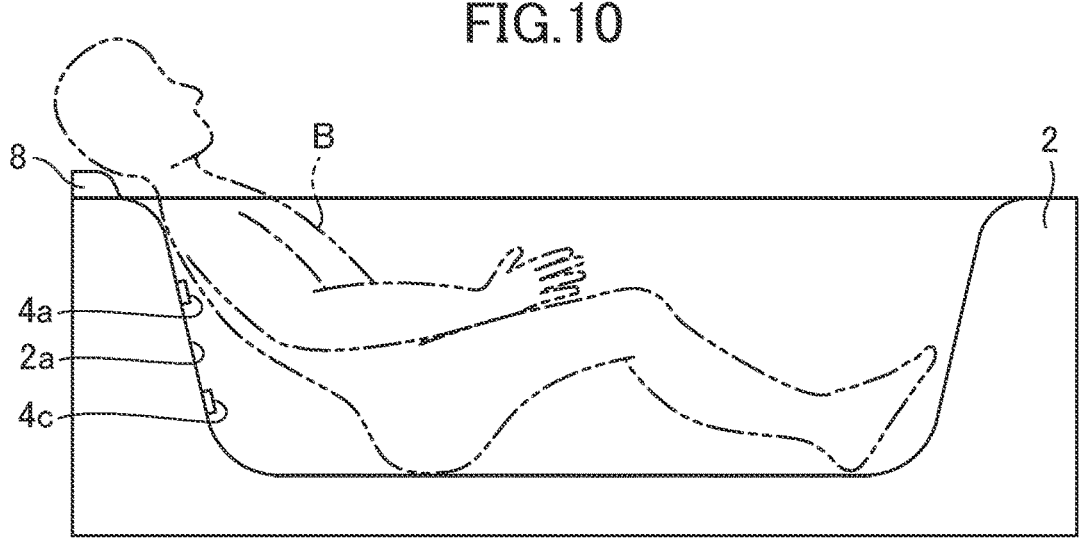
FIG. 10 is a diagram schematically showing a positional relationship between the body of the bathing person leaning against the backrest surface of the bathtub main body and each electrode attached to the backrest surface in the bathtub apparatus according to the embodiment of the present invention.

Next, effects of the bathtub apparatus 1 according to the embodiment of the present invention will be described with reference to FIGS. 6 to 10. FIG. 6 is a diagram showing an example of an electrocardiographic signal measured by the bathtub apparatus 1 according to the embodiment of the present invention. FIG. 7 is a diagram showing, as a comparative example, an example of an electrocardiographic signal that is affected by air bubbles. FIGS. 8 to 10 are each a diagram schematically showing a positional relationship between a body B of a bathing person leaning against the backrest surface 2*a* of the bathtub main body 2 and each electrode attached to the backrest surface 2*a*.

First, the water discharge device 8 may be operated by the bathing person by operating the remote control 6*a* (FIG. 1) attached to the wall surface of the bathroom R. When the water discharge device 8 is operated, hot water that is strip-shaped is discharged from the water discharge port 8*a* provided above the backrest surface 2*a* of the bathtub main body 2, toward shoulders of the bathing person leaning against the backrest surface 2*a*. A warming effect and a massaging effect on the bathing person may be obtained by discharge of hot water from the water discharge device 8. Furthermore, an electrocardiographic signal detection function may be activated by operation of the remote control 6a by the bathing person. The electrocardiographic signal that is detected is displayed on the display unit of the remote control 6a and the display device (not shown) outside the bathroom R.

FIG. 6 is an example of the electrocardiographic waveform that is detected by the bathtub apparatus 1 of the embodiment of the present invention. As shown in FIG. 6, an electrocardiographic waveform is a time-series waveform where a peak appears at a certain time cycle, and in the case where the electrocardiographic waveform is appropriately measured, an electrocardiographic waveform having sufficient RS amplitude at a peak is acquired. Furthermore, the heart rate of the bathing person may be determined based on the time cycle when the peak appears in the electrocardiographic waveform. The bathing person may objectively check that there are no abnormalities in his/her health state, by looking at the electrocardiographic waveform or the heart rate displayed on the remote control 6a. Moreover, it is possible to objectively grasp a change in the electrocardiographic waveform or the heart rate that is caused by an excessively long time of bathing in the hot water that is discharged from the water discharge device 8. Alternatively, when a family member or the like of the bathing person watches the electrocardiographic waveform or the heart rate displayed on the display device (not shown) installed outside the bathroom R, a change in the health state of the bathing person may be swiftly checked, and accidents and the like during bathing may be prevented.

Furthermore, in the present embodiment, the negative electrode 4a and the positive electrode 4b are arranged on the surface of the backrest surface 2a, at positions closer to the backrest surface 2a than the position P where the water that is discharged from the water discharge device 8 hits the water surface WL of the water stored in the bathtub main body 2. Accordingly, even in a case where the electrocardiographic signal is detected while water is being discharged from the water discharge device 8, the detection signal is not easily affected by air bubbles generated by hitting of water, and a desirable electrocardiographic waveform as shown in FIG. 6 is obtained. That is, water that is discharged from the water discharge device 8 flows into the bathtub main body 2, and air bubbles are generated at this time. However, in a state where the bathing person is leaning against the backrest surface 2a, many air bubbles flow in a direction away from the backrest surface 2a, and not many air bubbles flow toward the backrest surface 2a. Accordingly, the detection signal detected by the negative electrode 4a, the positive electrode 4b, and the reference electrode 4c arranged on the backrest surface 2a is not easily affected by the air bubbles, and a desirable electrocardiographic waveform may be obtained.

In contrast, as a comparative example, an example of the electrocardiographic signal that is greatly affected by air bubbles that are generated is shown in FIG. 7. As shown in FIG. 7, when the electrocardiographic signal is greatly affected by air bubbles that are generated by hitting of water, potential as a reference for the electrocardiographic signal fluctuates, and the waveform is greatly disturbed. When the electrocardiographic signal is disturbed in the manner shown in FIG. 7, the heart rate or the like of the bathing person becomes difficult to calculate accurately based on the electrocardiographic signal, and accurate monitoring of the health state of the bathing person becomes difficult.

However, in the present embodiment, because the negative electrode 4a and the positive electrode 4b are provided on the backrest surface 2a, influence of generation of air bubbles may be effectively suppressed. However, because the negative electrode 4a and the positive electrode 4b are attached to the backrest surface 2a, the bathing person easily comes into contact with the negative electrode 4a and the positive electrode 4b. If the bathing person in the bathtub main body 2 directly contacts one of the electrodes, an appropriate electrocardiographic waveform as shown in FIG. 6 cannot be obtained. In the present embodiment, the negative electrode 4a, the positive electrode 4b, and the reference electrode 4c are all attached to and exposed on the backrest surface 2a where the bathing person leans against. However, because a curvature of a corner portion of the bathtub is greater than a curvature of the bathing person, from back to shoulders, there is a space between the bathtub and the bathing person. By arranging the electrodes in this space, back and shoulders of the bathing person may be prevented from coming into contact with each electrode.

FIGS. 8 to 10 are each a diagram schematically showing a positional relationship between the body B of the bathing person leaning against the backrest surface 2a of the bathtub main body 2 and each electrode attached to the backrest surface 2a. As shown in FIG. 8, in a case where the bathing person leans against a center of the backrest surface 2a, the body B of the bathing person contacts the backrest surface 2a between the negative electrode 4a and the positive electrode 4b, and the bathing person does not come into contact with the negative electrode 4a and the positive electrode 4b. That is, in the present embodiment, the distance between the negative electrode 4a and the positive electrode 4b in the horizontal direction is about 380 mm, and this distance is greater than an average width between the anterior axillary lines of adult males, and thus, normally, the body B of the bathing person does not come into contact with the negative electrode 4a and the positive electrode 4b.

Additionally, in plan view, the backrest surface 2a of the bathtub main body 2 is curved in a manner protruding outward, and when the bathing person unconsciously leans against the backrest surface 2a, the body B of the bathing person is naturally positioned at approximately center of the backrest surface 2a in a width direction. Furthermore, the reference electrode 4c is attached to the center of the backrest surface 2a but is attached to a low position on the backrest surface 2a (FIG. 3), and the reference electrode 4c does not usually come into contact with the body B of the bathing person. That is, when the bathing person leans against the backrest surface 2a without thinking, the back of the bathing person is separated from the backrest surface 2a at a low position, and the reference electrode 4c and the bathing person do not come into contact with each other.

In contrast, in the case where the bathing person leans against a corner portion of the bathtub main body 2 in the manner shown in FIG. 9, the body B of the bathing person contacts the backrest surface 2a and a side wall surface 2c next to the backrest surface 2a across the positive electrode 4b but does not come into contact with the positive electrode 4b. In the same manner, in the case where the bathing person leans against a corner portion on an opposite side from the one shown in FIG. 9, the body B of the bathing person contacts the backrest surface 2a and a side wall surface 2d next to the backrest surface 2a across the negative electrode 4a but does not come into contact with the negative electrode 4a.

Furthermore, in the case where the bathing person deeply leans against the backrest surface 2a of the bathtub main body 2 (with the shoulders at low positions) in the manner shown in FIG. 10, the neck of the bathing person contacts an upper end of the backrest surface 2a and the buttocks of the bathing person contacts the bottom surface of the bathtub main body 2 across each electrode. Accordingly, in the case where the bathing person leans deeply, the back of the bathing person hardly contacts the backrest surface 2a, and the body B of the bathing person does not come into contact with the negative electrode 4a, the positive electrode 4b, and the reference electrode 4c.

As described above, the negative electrode 4a, the positive electrode 4b, and the reference electrode 4c are arranged exposed on the backrest surface 2a of the bathtub main body 2, but the body B of the bathing person does not normally come into contact with each electrode in a state where the bathing person is naturally leaning against the backrest surface 2a. Accordingly, the electrocardiographic signal of the bathing person may be appropriately acquired.

With the bathtub apparatus 1 of the embodiment of the present invention, the negative electrode 4a, the positive electrode 4b, and the reference electrode 4c are arranged closer to the backrest surface 2a than the position P where water that is discharged from the water discharge device 8 hits the water surface WL of water that is stored in the bathtub main body 2 (FIG. 2). Accordingly, the electrocardiographic signal may be satisfactorily detected also by the bathtub apparatus 1 including the water discharge device 8 that discharges water toward the inside of the bathtub main body 2.

Furthermore, with the bathtub apparatus 1 of the present embodiment, the negative electrode 4a and the positive electrode 4b are arranged on the inner wall surface of the bathtub main body 2, at height positions of about 300 mm from the bottom surface. Moreover, the negative electrode 4a and the positive electrode 4b are arranged closer to the backrest surface 2a than the position P where the water hits the water surface WL of the water stored in the bathtub main body 2 in a state where the water surface WL is at a height position of about 300 mm. With the bathtub apparatus 1 of the present embodiment, the negative electrode 4a and the positive electrode 4b are at least partially under water in the bathtub main body 2 at all times, and thus, the electrocardiographic signal may be more reliably acquired by the electrodes. Moreover, according to the present embodiment, the water surface WL does not easily fall below the electrodes even when the water surface WL inside the bathtub main body 2 is rippled, and disturbance in the electrocardiographic signal due to the water surface WL falling below the electrodes may be prevented.

Furthermore, with the bathtub apparatus 1 of the present embodiment, the negative electrode 4a, the positive electrode 4b, and the reference electrode 4c are arranged on the backrest surface 2a, at positions within 360 mm from the water discharge port 8a of the water discharge device 8 in the horizontal direction, and influence of air bubbles generated by water hitting the water surface may be reliably suppressed.

Furthermore, with the bathtub apparatus 1 of the present embodiment, a pair of electrodes including the positive electrode 4b and the negative electrode 4a is arranged on the backrest surface 2a forming a short side of the bathtub main body 2, and thus, a distance between the bathing person and each electrode does not become excessively great even in the case of application to a large bathtub main body 2, and an electrocardiographic signal with sufficient amplitude may be detected.

Moreover, with the bathtub apparatus 1 of the present embodiment, the reference electrode 4c is also arranged on the backrest surface 2a where the positive electrode 4b and the negative electrode 4a are arranged, and thus, surfaces where the electrodes are arranged may be put together into one surface, and electric wiring connected to each electrode may be shortened, and S/N ratio of the detection signal may be improved. Moreover, because the electrodes are assembled and attached to the backrest surface 2a, ease of assembly at the time of manufacturing the bathtub main body 2 may be increased, and ease of maintenance may also be increased.

Moreover, with the bathtub apparatus 1 of the present embodiment, the positive electrode 4b and the negative electrode 4a are each arranged away from the center line C, and the positive electrode 4b and the negative electrode 4a may be arranged on both sides of the heart of the bathing person leaning against the backrest surface 2a of the bathtub main body 2, and an electrocardiographic signal with sufficient amplitude may be acquired.

Moreover, with the bathtub apparatus 1 of the present embodiment, the distance between the positive electrode 4b and the negative electrode 4a in the left-right direction is 700 mm or less, and an electrocardiographic signal with sufficient amplitude may be acquired in relation to a regular bathing person or normal electrical conductivity of water.

Moreover, with the bathtub apparatus 1 of the present embodiment, the distance between the positive electrode 4b and the negative electrode 4a in the left-right direction is set to 380 mm or more, and thus, a regular bathing person may be effectively prevented from coming into contact with the electrodes when the bathing person leans against the backrest surface 2a with a normal posture.

An embodiment of the present invention has been described above, but various changes may be made to the embodiment described above. Particularly, with the bathtub apparatus 1 of the embodiment described above, the negative electrode 4a, the positive electrode 4b, and the reference electrode 4c are provided on the backrest surface 2a. In contrast, as a modification, these electrodes may be arranged on an inner wall surface of the bathtub main body 2 other than the backrest surface 2a and may be arranged closer to the backrest surface 2a than the position P where water that is discharged from the water discharge device 8 hits the water surface of the water that is stored in the bathtub main body 2.

REFERENCE SIGNS LIST 1 bathtub apparatus
2 bathtub main body
2a backrest surface (first inner wall surface)
2b apron
2c side wall surface
2d side wall surface
4a negative electrode
4b positive electrode
4c reference electrode
6 signal processing apparatus
6a remote control
6b housing
8 water discharge device
8a water discharge port
10 electrode portion
10a disc portion
10b axial portion
12a front packing 12b rear packing
14 flange
16 moistureproof tube
18 connection terminal
20 fixing screw
22 electric lead
24 sheath
26 differential amplifier circuit
28 filter circuit
30 amplifier circuit
32 A/D converter
34 interface circuit

What is claimed is:

1. A bathtub apparatus capable of detecting an electrocardiographic signal, the bathtub apparatus comprising:
a bathtub main body that is formed into a substantially rectangular shape in plan view;
a water discharge device that discharges water toward inside of the bathtub main body, the water discharge device being provided above a first inner wall surface forming a short side of the bathtub main body; and
an electrode that is attached to the bathtub main body to detect an electrocardiographic signal of a bathing person via water that is stored in the bathtub main body;
wherein the electrode is fixed to a through hole formed in an inner wall surface of the bathtub main body, and is arranged closer to the first inner wall surface than a position where water that is discharged from the water discharge device hits a water surface of the water that is stored in the bathtub main body.

2. The bathtub apparatus according to claim 1, wherein the electrode is arranged on the inner wall surface of the bathtub main body, at a predetermined height position, and in a state where the water surface of the water that is stored in the bathtub main body is at the predetermined height position, the electrode is arranged closer to the first inner wall surface than the position where the water hits the water surface.

3. The bathtub apparatus according to claim 1, wherein the electrode is arranged at a position within 360 mm in a horizontal direction toward the inside of the bathtub main body from a water discharge port of the water discharge device.

4. The bathtub apparatus according to claim 1, wherein the electrode is arranged on the first inner wall surface.

5. A bathtub apparatus capable of detecting an electrocardiographic signal, the bathtub apparatus comprising:
a bathtub main body that is formed into a substantially rectangular shape in plan view; and
electrodes that are attached to the bathtub main body to detect an electrocardiographic signal of a bathing person via water that is stored in the bathtub main body;
wherein the electrodes are a pair of electrodes including a positive electrode and a negative electrode, and
wherein each of the pair of electrodes is fixed to a through hole formed in a first inner wall surface forming a short side of the bathtub main body, and the positive electrode and the negative electrode are arranged at respective positions on a left side and a right side of a center line passing through a center of the first inner wall surface in a horizontal direction.

6. The bathtub apparatus according to claim 5, further comprising a reference electrode to detect a reference potential, the reference electrode being arranged on the first inner wall surface.

7. The bathtub apparatus according to claim 5, wherein the positive electrode and the negative electrode are each arranged on the first inner wall surface, away from the center line in a left-right direction.

8. The bathtub apparatus according to claim 7, wherein a distance between the positive electrode and the negative electrode in the left-right direction is 700 mm or less.

9. The bathtub apparatus according to claim 7, wherein a distance between the positive electrode and the negative electrode in the left-right direction is 380 mm or more.

* * * * *